United States Patent [19]
Yamada et al.

[11] Patent Number: 5,499,909
[45] Date of Patent: Mar. 19, 1996

[54] PNEUMATICALLY DRIVEN MICRO-PUMP

[75] Inventors: Takahiro Yamada; Shinji Ando; Yoshihiro Naruse, all of Ichikawa, Japan

[73] Assignees: Aisin Seiki Kabushiki Kaisha of Kariya, Kariya; Kabushiki Kaisha Shinsangyokaihatsu, Tokyo, both of Japan

[21] Appl. No.: 341,071

[22] Filed: Nov. 17, 1994

[30] Foreign Application Priority Data

Nov. 17, 1993 [JP] Japan .................................. 5-287190
Nov. 17, 1993 [JP] Japan .................................. 5-287191

[51] Int. Cl.⁶ .................................................. F07B 43/06
[52] U.S. Cl. .................... 417/384; 417/413.1; 417/395; 417/266
[58] Field of Search .......................... 417/339, 384, 417/389, 395, 244, 266, 254, 479, 413.1; 604/131, 153

[56] References Cited

U.S. PATENT DOCUMENTS

| | | | |
|---|---|---|---|
| 2,383,193 | 8/1945 | Herbert | 417/317 |
| 2,821,930 | 2/1958 | Smith | 417/317 |
| 2,959,131 | 11/1960 | Smoosmith | 417/395 |
| 3,148,624 | 9/1964 | Baldwin | 417/339 |
| 4,265,601 | 5/1981 | Mandroian | 417/479 |
| 4,559,038 | 12/1985 | Berg et al. | 604/153 |
| 4,565,542 | 1/1986 | Berg | 604/131 |
| 4,583,920 | 4/1986 | Lindner | 417/266 |
| 4,650,469 | 3/1987 | Berg et al. | 604/131 |
| 4,687,423 | 8/1987 | Maget et al. | 417/395 |
| 5,018,949 | 5/1991 | Gotz | 417/339 |
| 5,171,132 | 12/1992 | Miyazaki et al. | 417/413 |

FOREIGN PATENT DOCUMENTS

| | | | |
|---|---|---|---|
| 3225086 | 10/1991 | Japan . | |
| 566822 | 9/1993 | Japan . | |
| 6-173856 | 6/1994 | Japan | 417/395 |
| 6-257570 | 9/1994 | Japan | 417/395 |

*Primary Examiner*—Richard A. Berisch
*Assistant Examiner*—Peter G. Korytnyk
*Attorney, Agent, or Firm*—Sughrue, Mion, Zinn, Macpeak & Seas

[57] ABSTRACT

A micro-pump is disclosed for pneumatically causing a bulging/retracting motion of a plurality of micro-diaphragms disposed in an array along a channel through which a fluid is being driven. The pump includes channel means (10) including a first port (11), a second port (12) and a flow-through space (13) providing a communication therebetween; a plurality of diaphragms (21a–21e) disposed in an array along the flow-through space (13); diaphragm support means (20) including a plurality of actuating gas spaces (22a–22e) which opposes the rear surfaces of the respective diaphragms; a plurality of reciprocatory motion means for individually imparting an oscillation of pneumatic pressure to the respective actuating gas spaces (22a–22e), and drive means for driving the reciprocatory motion means for driving motion with phase differences therebetween so that the upper dead center shifts in the direction of the array.

18 Claims, 7 Drawing Sheets

PNEUMATICALLY DRIVEN MICRO-PUMP

FIELD OF THE INVENTION

The invention relates to a micro-pump (or miniature pump) which feeds and drives a fluid at a low rate (flow rate per unit time), and in particular, to a low flow rate pump which is less susceptible to pressure impact as a result of a pumping operation.

BACKGROUND OF THE INVENTION

In an artificial dialysis, for example, which requires monitoring blood which is fed to a dialysis system from a living body or blood which is returned from the system to the body, it is preferred to provide a continuous monitoring. In this instance, it becomes necessary to bleed the blood from the path of dialysis so as to be fed to a monitoring unit. Since blood which is added with a reagent or the like in a monitoring unit is discarded or disposed, it is desirable for the purpose of the continuous monitoring that the blood be continuously fed to the monitoring unit at a speed of flow which is as low as possible. It is also desirable that oscillations in the pressure, in particular, a pressure of impact be minimized in order to prevent thrombus from being formed and to increase the accuracy of measurement or study. It will be appreciated that the need for a continuous feeding at a low speed of flow with reduced oscillation of pressure also exists when injecting a very small amount of medicine or assisting liquid into the living body continuously.

To meet such requirements, a roller pump has been proposed in the art in which a pressure is applied to an elastic tube by a roller which is mounted on the distal end of a rotor comprising three or four radially extending rotary arms. A finger pump is also proposed in which a plurality of pressure plates are disposed along the direction in which the elastic tube extends, with each of the pressure plates being driven to project by a cam plate which is driven for rotation by an electric motor so that an array of cam plates produces a peristaltic motion in the tube to squeeze it for feeding a fluid located therein.

With either roller pump or finger pump, a fluid being driven is withdrawn into the tube by the restoring force of the tube as a pressure is applied to the elastic tube, and this involves a limit in principle on the flow rate which can be reduced. If a tube of a smaller diameter is employed in order to provide a reduced flow rate, there occurs a greater variation in the flow rate established, as a result of dimensional error of the tube itself or errors caused when mounting the roller or pressure plates, thus resulting in a difficulty in adjusting the flow rate. In addition, as the elasticity of the tube is degraded, the flow rate being delivered will be reduced, and a variation in the flow rate is likely to occur. Also, the ability of the tube which accommodates for a pressure impact by its own resilience will be degraded.

SUMMARY OF THE INVENTION

It is a first object of the invention to reduce a pressure impact, a second object to provide an exact and low flow rate, and a third object to facilitate an adjustment of the flow rate being delivered.

A pneumatically driven micro-pump according to the invention comprises channel means (10) including a first port (11), a second port (12) and a flow-through space (13) disposed therebetween in communication therewith; a plurality of diaphragms (21a–21e) disposed in an array along the flow-through space (13) in a direction from the first port (11) to the second port (12) and each having its front surface exposed to the flow-through space (13) and capable of bulging/retracting with respect to the space; diaphragm support means (20) disposed on the opposite side of the diaphragms (21a–21e) from the flow-through space (13) and including a plurality of actuating gas spaces (22a–22e) which are disposed in opposing relationship with each of the back surfaces of the respective diaphragms; a plurality of reciprocatory motion means (60, 73a–73e in FIG. 1; 53a–53e and 55 in FIG. 4; and 60, 75a–75e, 76a–76e in FIG. 5) for individually imparting pneumatic pressure oscillation to each of the actuating gas spaces (22a–22e); and drive means (72a–72e, 90a–90e and 100 in FIG. 1; 72a–72e, 90a–90e and 100 in FIG. 4; and 96, 97 in FIG. 5) for driving respective reciprocatory motion means for reciprocatory motion with phase differences therebetween such that an upper dead center where a high pressure peak is applied to the actuating gas space (22a–22e) shifts in a direction from one nearest the first port (11) toward another nearest the second port (12).

It should be noted that reference numerals and characters appearing in parentheses in the above description designate corresponding elements used in embodiments shown in the drawings and described later.

When the drive means drives the individual reciprocatory motion means for reciprocatory motion with phase differences therebetween such that the upper dead center where a high pressure peak is applied to the associated actuating gas space (22a–22e) is applied shifts in a direction from one nearest the first port (11) toward another nearest the second port (12), the pressures within the actuating gas spaces (22a–22e) oscillate between high and low levels, and the high pressure peak sequentially shifts from the actuating gas space (22a) located nearest the first port (11) to the actuating gas space (22b) located nearest the second port (12). In response to the pressure oscillation occurring in the actuating gas spaces (22a–22e) in this manner, the diaphragms (21a–21e) located in the high pressure zone bulge with respect to the flow-through space (13) while they retract from the flow-through space (13) in the low pressure zone. Accordingly, the bulging action sequentially shifts from the diaphragm (21a) located nearest the first port (11) to the diaphragm (21b) located nearest the second port (12). In this manner, the fluid present within the flow-through space (13) is squeezed in a direction from the first port (11) toward the second port (12).

Since there is the actuating gas spaces (22a–22e) between the reciprocatory motion means and the diaphragms and since the gas within the spaces, which is air, is compressible, namely, subject to shrinkage and expansion in response to an increase or a decrease in the pressure, if the reciprocatory motion means undergo a reciprocatory motion in a pulse manner or moving between two positions, the resulting pressure applied to the diaphragm is smoothed into a sinusoidal wave as a result of shrinkage/expansion of the gas, whereby the bulging/retracting motion of the diaphragms (21a–21e) with respect to the actuating gas spaces (22a–22e) will be smooth and gentle, with consequence that the fluid being delivered cannot produce any substantial pressure oscillation or pressure impact of a frequency region which is higher than that of the reciprocatory motion of the diaphragms. Accordingly, the fluid will be delivered more in the nature of a static flow.

Since the gases in the actuating gas spaces (22a–22e) is compressible, no peaking pressure is applied to the diaphragms, thus reducing the probability that the diaphragms be destroyed under the influence of a pressure impact. This allows the diaphragms to be constructed as a thin member of a reduced size, which in turn allows a low flow rate to be achieved. Nevertheless no substantial fluctuation occurs in the flow rate and still an adjustment of the flow rate is allowed by adjusting the period of repetition of the oscillation of the reciprocatory motion means. In this manner, a micro-pump which provides a required low flow rate, which is adjustable, is provided. Because the diaphragms do not produce any aging effect in their configurations, as experienced with a tube used in the roller pump described above, there is no substantial reduction in the flow rate being delivered with time.

Other objects and features of the invention will become apparent from the following description of embodiments with reference to the drawings.

DESCRIPTION OF PREFERRED EMBODIMENTS

First Embodiment

Figure 1:
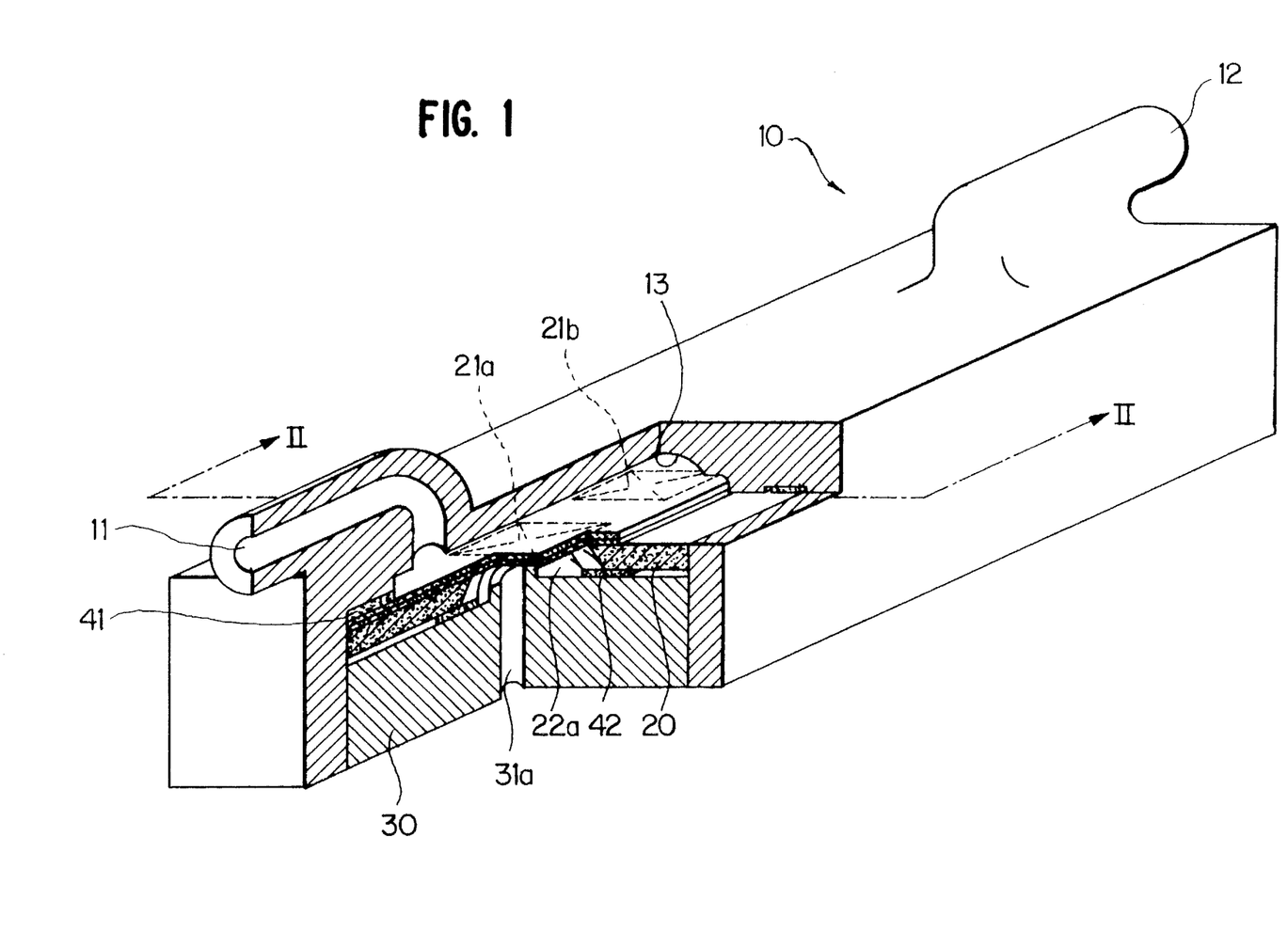
FIG. 1 is a perspective view, partly broken away, showing the appearance of a fluid feed head according to a first embodiment of the invention.
Figure 2:
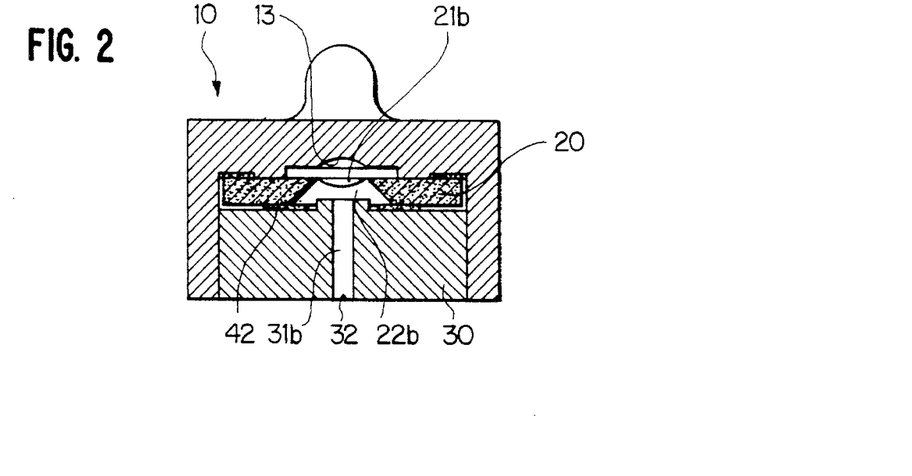
FIG. 2 is a cross section taken along the line II—II shown in FIG. 1.
Figure 3:
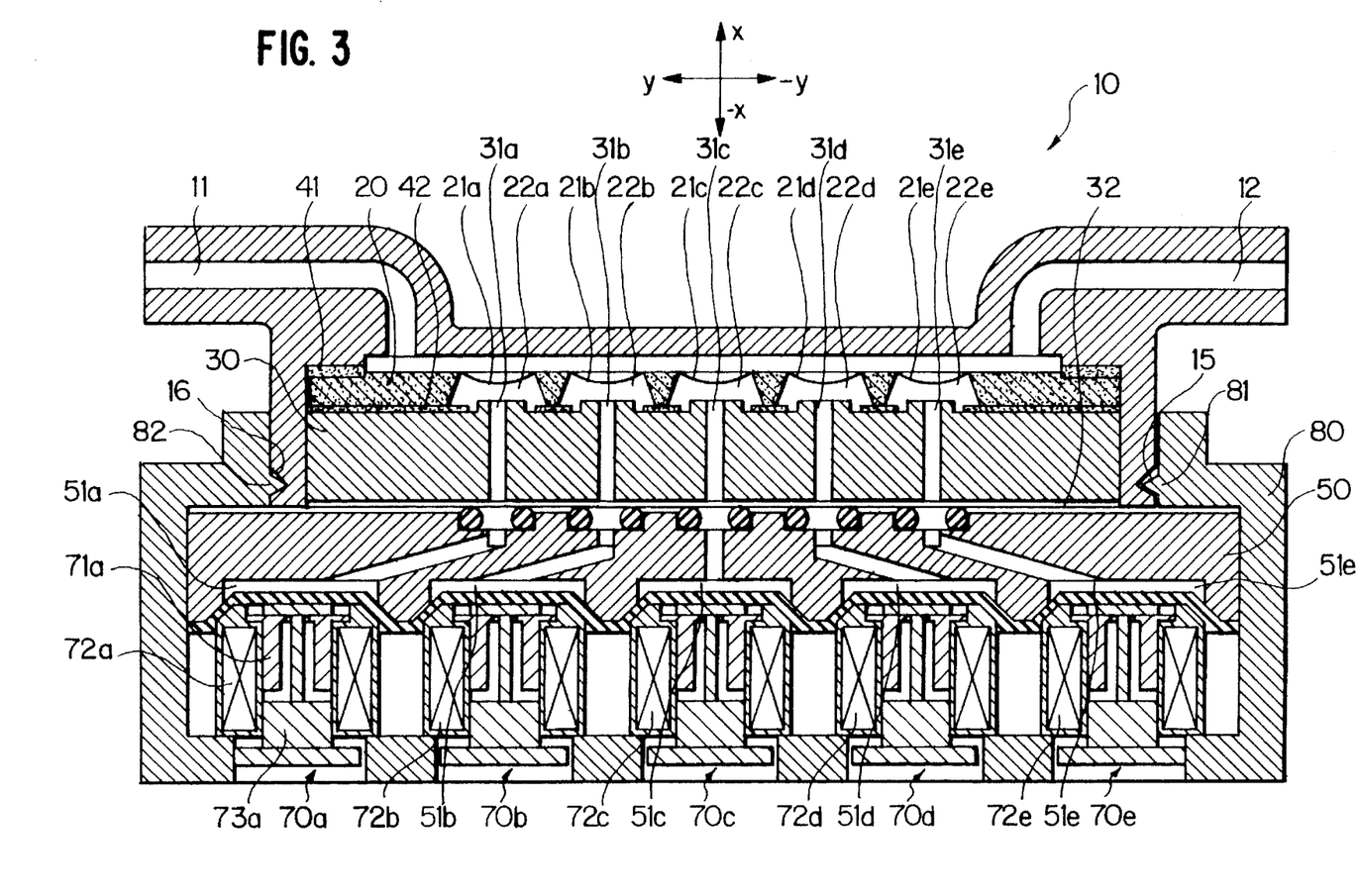
FIG. 3 is a longitudinal section of the entire first embodiment incorporating the fluid feed head shown in FIG. 1.

FIG. 1 shows the appearance of a fluid feed head according to a first embodiment of the invention, partly broken away; and FIG. 2 shows a cross section taken along the line II—II. A longitudinal section is illustrated in FIG. 3 which shows the entire pump according to the first embodiment. A channel member 10 is substantially in the form of a rectangular box, and a flow-through groove 13 having an inner space which can be described as part of the periphery of a cylinder which is cut along an elongate axis is formed in the inner surface of a bottom wall of the channel member 10. As viewed in cross section, the bottom surface of the flow-through groove 13 is arcuate in configuration as shown in FIG. 2. The left end of the flow-through groove 13 communicates with a first port 11 while its right end communicates with a second port 12. A substantially rectangular silicon plate 20 is inserted inside the channel member 10, and is adhesively secured to the bottom surface of the channel member 10 through a heat melting adhesive film 41 interposed therebetween. The silicon plate 20 is formed with five actuating gas chambers 22a–22e, as by an etching process, at locations opposite to the flow-through groove 13. An opening of each of these gas chambers 22a–22e which faces the flow-through groove 13 is closed by one of diaphragms 21a–21e. In the present embodiment, the silicon plate 20 including the gas chambers 22a–22e and the diaphragms 21a–21e are manufactured in a manner mentioned below.

(a) A silicon plate having a thickness on the order of 250 μm is formed with $SiO_2$ layers on the front and rear surfaces thereof (although a plurality of silicon plates 20 are used, a single silicon plate from which such plurality of silicon plates 20 are formed will be described herein). The silicon plate is then baked at a temperature on the order of 1,200° C. in order to provide a sag in a diaphragm which is to be formed later, thus forming $SiO_2$ layer, (the layer on the front surface will provide a base layer for the diaphragm to be formed later) having a thickness on the order of 5,000 Å.

(b) NiCrSi layer having a thickness on the order of 2,000 Å is formed, by a sputtering technique, on the $SiO_2$ layer formed on the front surface of the silicon plate. Part of NiCrSi layer provides an upper layer of the diaphragm at a later stage. To maintain a sag in the diaphragm until the formation of NiCrSi layer is completed, the silicon plate is maintained at a temperature on the order of 1,200° C.

(c) After the silicon plate is cooled down to a normal temperature, a resist film is formed on top of NiCrSi layer, and is then exposed and etched to leave the resist film only in the region of diaphragms (21a–21e).

(d) NiCrSi layer is removed except where it is located directly below the resist film, by a dry etching (or reverse sputtering). The NiCrSi layer which remains after such etching process and the $SiO_2$ layer which is located directly below it define a diaphragm as a two layer construction. As a result of the temperature decrease, these two layers tend to shrink, thereby generating internal stresses of a relatively large magnitude therein. Because of differences in the coefficient of thermal expansion, the $SiO_2$ layer undergoes compressive stresses while the NiCrSi layer undergoes tensile stresses. However, since they are integral with the base of the silicon plate at this state, there occurs no sag therein.

(e) The resist film which remains on top of NiCrSi layer is removed to expose the latter, and resist films are again formed on the front and the rear surfaces thereof in order to form the actuating gas chambers 22a–22e.

(f) Openings for the actuating gas chambers 22a–22e are formed in the rear surface of the silicon plate at locations opposite to the NiCrSi layer 22, by exposure and etching process, and $SiO_2$ layer in the region of such openings (formed in the rear surface of the silicon plate 20) are etched off, followed by removal of the resist films on both the front and the rear surface.

(g) An opening is etched in the $SiO_2$ layer on the rear surface to form a hole which reaches the $SiO_2$ layer on the front surface or the lower layer of the diaphragm, which is one of the actuating gas chambers 22a–22e. Upon completion of the etching process, the diaphragm comprising the $SiO_2$ layer and the NiCrSi layer is freed from constraint, whereby the compressive stresses acting on the $SiO_2$ layer is released to produce a sag in the diaphragm.

(h) $SiO_2$ layers on the front and the rear surface are removed and the silicon plate is severed and separated into a plurality of rectangular units. One of the separate pieces is shown as a silicon plate 20 in FIG. 3.

Returning to FIGS. 1 and 2, an upper relay plate 30 is adhesively secured, under pressure, to the lower surface of the silicon plate 20 through an interposed heat fusing adhesive film 42. The upper relay plate 30 is formed with gas passages 31a–31e which communicate with the actuating gas chambers 22a–22e, and a fine groove 32 (FIG. 2) is formed in the lower surface of the relay plate 30 so as to pass through the center of one of the gas passages 31a–31e. The groove 32 has a narrow width and a narrow depth as may be formed by scratching with a pin point and which cannot be blocked by an O-ring (which is disposed in abutment against the upper relay plate 30 in FIG. 3).

As discussed, the silicon plate 20 and the upper relay plate 30 are sequentially inserted, in the order named, into the channel member 10, and these three members 10, 20 and 30 are integrally secured together to form a fluid feed head.

FIG. 3 shows a micro-pump in which the fluid feed head mentioned above is assembled. A lower case 80 connected to the upper relay plate 30 is generally box shaped and is open at its top while its bottom wall is formed with openings which permit a vertical movement of plungers 73a–73e therein. Solenoids 70a–70e are contained in the lower case 80 and are referenced to these openings. A solenoid 70a comprises a core 71a, an electrical coil 72a which is disposed thereon and a plunger 73a. The plunger 73a has a portion of a reduced diameter which extends through the core 71a, and also includes a disc-shaped abutment head located outside the core 71a, with the abutment head being integral with the plunger 73a together with the portion of the reduced diameter. The remaining solenoids 70b–70e are similarly constructed and dimensioned as the solenoid 70a. A thin film 60 of silicone rubber is placed on top of the abutment head of the solenoids 70a–70e, and a lower relay plate 50 is placed on top of the thin film 60. The lower relay plate 50 is formed with gas chambers 51a–51e which allow the abutment heads of the solenoids 70b–70e to push up the thin film 60, gas passages which allow a communication of these gas chambers 51a–51e with the gas passages 31a–31e, and openings, which receive O-rings, for providing a substantially hermetic coupling between the gas passages 31a–31e in the upper relay plate 30 and the gas passages 31a–31e in the lower relay plate 50.

As discussed, five solenoids 70a–70e, the thin film 60 and the lower relay plate 50 are received sequentially from bottom, in the sequence named, within the lower case 80. By pushing the channel member 10 in which the silicon plate 20 and the relay plate 30 are assembled in the manner mentioned above into the top opening of the lowercase 80, the upper relay plate 30 acts through the O-rings to press the lower relay plate 50 down, thereby pushing the thin film 60, and in turn the solenoids 70a–70e against the inner bottom surface of the lower case 80. Under this condition, claws 81, 82 formed on the lower case 80 snap into notched grooves 15, 16 formed in the lateral sides of the channel member 10, thereby integrally connecting the channel member 10 and the lower case 80 together.

When the channel member 10 is forcibly pulled upward relative to the lower case 80, the claws 81, 82 become disengaged from the notched grooves 15, 16, allowing the channel member 10 to be separated from the lower case 80. The purpose of such detachable coupling is to enable a disposal thereof when using the described arrangement as a medical infutation pump in order to prevent an infection from occurring.

When mounting the channel member 10 upon the lower case 80, as the upper relay plate 30 is further pressed down subsequent to its tight engagement with the O-rings, there occurs a pressure rise in the space of gas (which is air in the present embodiment) comprising the gas chambers 51a–51e and the actuating gas chambers 22a–22e to cause the diaphragms 21a–21e to remain in their bulging positions, or if such bulging action does not occur, a subsequent temperature rise may cause a pressure rise in the described space to cause a bulging of the diaphragms 21a–21e. If the plunger 73a is driven upward when the diaphragms are bulging in this manner, a further pressure rise in the above space may occur, causing a rupture of the diaphragm 21a. If a rupture does not occur, the bulging/retracting stroke of the diaphragm 21a in response to the reciprocatory motion of the plunger 73a may be reduced, thus significantly degrading the pumping capacity. To prevent such phenomena from occurring, the fine grooves 32e are formed in the upper relay plate 30. If the air pressure in the space comprising the gas chambers 51a–51e and the actuating gas chambers 22a–22e rises above the atmospheric pressure in response to a further depression of the upper relay plate 30 which continues after its tight engagement with the O-rings when mounting the channel member 10 upon the lower case 80, there is formed a path for the air in the described space to be vented, the path including the fine grooves 32, a gap between the upper and the lower relay plate 30, 50, and a gap between the channel member 10 and the lower case 80. A venting path is also formed between the space and the atmosphere through a similar path if a temperature rise or drop causes a temperature rise or drop in the described space after the channel member 10 has been mounted upon the lower case 80. Accordingly, it is assured that the diaphragms 21a–21e maintain a given sagged configuration (see FIG. 3) when not in use.

When not in use, the diaphragms 21a–21e assume a sagged configuration as shown in FIGS. 2 and 3 at normal temperatures, as a result of a baking of the silicon plate which occurs during the time the $SiO_2$ layer is formed. If a temperature rise occurs in the gas chambers 22a–22e under this condition, the diaphragms will bulge in a direction to extend into the flow-through groove 13, tightly contacting the bottom surface of the flow-through groove 13. Assuming that the flow-through groove 13 is shaped to exhibit a rectangular cross section, as the bulging top of the diaphragm abuts against the planar bottom surface of the flow-through groove 13, the diaphragm top will be deformed from its normal spherical configuration into a planar configuration. In this manner, the diaphragm may be repeatedly subject to a folding distortion to reduce its useful life. Alternatively, as the diaphragm bulges, a substantially triangular clearance may be formed between the corner of the bottom and the diaphragm, and such clearance may allow the pressure to be passed from the downstream to the upstream side, thereby reducing the efficiency of delivery. However, when the flow-through groove 13 is arcuate in cross section, no folding distortion is caused which assures an increased useful life of the diaphragm while maintaining a high pumping efficiency, namely, as considered in terms of the amount of fluid being driven relative to the oscillation of the diaphragm.

Figure 4:
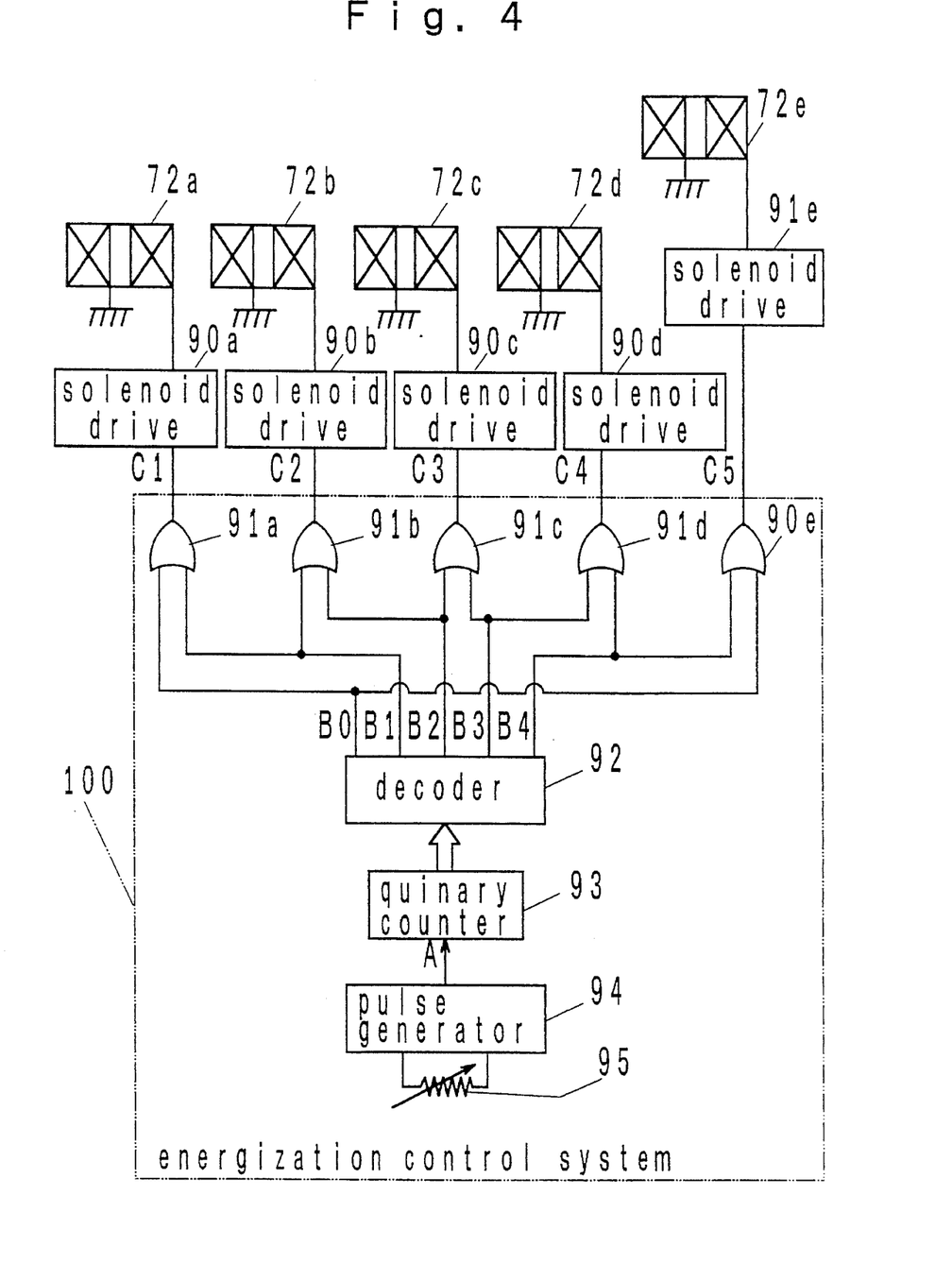
FIG. 4 is a block diagram of an electrical circuit which energizes electrical coils 72a–72e shown in FIG. 3.

FIG. 4 shows an electrical circuit which energizes the electrical coils 72a–72e of the solenoids 70a–70e to cause an oscillation of the diaphragms 21a–21e. An energization control system 100 includes a pulse generator 94, which produces an electrical pulse A having a period which corresponds to the resistance of a potentiometer 95. Electrical signals produced by the circuit elements of the system 100 are graphically shown in FIG. 5. A quinary counter 93 counts such electrical pulses A. The counter 93 is a cyclic counter which counts up every pulse A from an initial condition of the count 0 and which is automatically reset to a count 0 upon reaching a count of 5, and again counting up to 1, 2, - - - . Count data from 0 to 5 is applied to a decoder 92, an output signal B0 of which is maintained at a high level H while the remaining output signals B1–B4 are maintained at a low level L as long as the count data is equal to 0. When count data is equal to one of 1 to 4, a corresponding one of output signals B1 to B4 assumes an H level while the remaining signals are maintained at an L level. Adjacent ones of the output signals B0–B4 which are adjacent to each other in the sequence the H level is produced are applied to OR gates 91a–91e, respectively, the outputs of which are shown as signals C1–C5 in FIG. 5, which are applied to solenoid drivers 90a–90e, respectively. Each of the solenoid drivers 90a–90e energizes a corresponding one of the electrical coils 72a–72e as long as the associated signals C1–C5 assume an H level.

Figure 5:
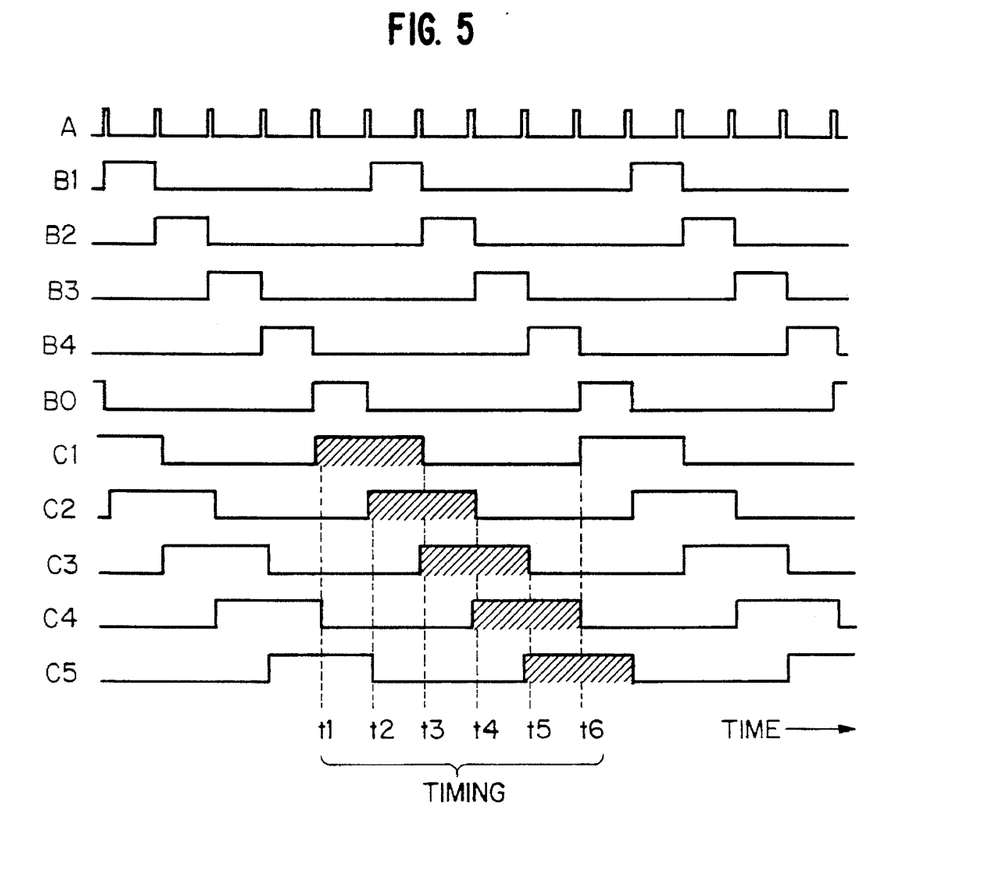
FIG. 5 is a series of timing charts illustrating various electrical signals appearing at selected points within an energization control circuit 100 shown in FIG. 4.

By way of example, when the electrical coil 72a is energized (C1=H) at time t1 shown in FIG. 5, the plunger 73a is attracted by the core 71a, whereby the abutment head at the top end of the plunger 73a pushes up the thin film 60 inward of the gas chamber 51a. This acts through the gas passage 31a to cause a pressure rise in the actuating gas chamber 22a, whereby the diaphragm 21a changes from its sagged configuration (see FIGS. 2 and 3) to a bulged configuration projecting into the flow-through groove 13. Thus, the diaphragm 21a bulges into the fluid channel 13. As a result, fluid being driven which is located on top of the diaphragm 21a is partly driven in the direction of the first port 11 and partly driven in the direction of the diaphragm 21b.

At subsequent time t2, the diaphragm 21a continues to be bulging, but the electrical coil 72b begins to be energized, whereby the diaphragm 21b bulges into the fluid channel 13 in the same manner as mentioned above. At this time, the fluid being driven which is located on top of the diaphragm 21b will be, substantially in its entirety, driven in the direction of the diaphragm 21c since the diaphragm 21a remains as bulged.

At time t3, the electrical coil 72a ceases to be energized, whereby the plunger 73a will be driven downward by the resilience of the thin film 60, whereby the chamber 51a assumes a negative pressure, causing the diaphragm 21a to retract. At this time, fluid being driven which is located in the input port 11 is withdrawn by the diaphragm 21a. Because the diaphragm 21b assumes its bulged position, the fluid which is located on top of the diaphragm 21b is not substantially attracted. At time t3, the energization of the electrical coil 72c is initiated, and the diaphragm 21c bulges into the fluid channel 13 in the same manner as mentioned above. At this time, fluid located on top of the diaphragm 21c will be driven, substantially in its entirety, toward the diaphragm 21d, because the diaphragm 21b assumes its bulged position.

At time t4, the electrical coil 72b ceases to be energized, whereby the plunger 73b is driven downward under the resilience of the thin film 60, causing the chamber 51b to assume a negative pressure to cause the diaphragm 21b to retract. At this time, fluid located on top of the diaphragm 21a will be attracted by the diaphragm 21b. Since the diaphragm 21c assumes its bulged position, fluid on top of the diaphragm 21c is not substantially attracted. At time t4, the energization of the electrical coil 72d is initiated to cause the diaphragm 21d to bulge into the fluid channel 13 in the same manner as mentioned above. Fluid located on top of the diaphragm 21d is driven, substantially in its entirety, toward the diaphragm 21e since the diaphragm 21c assumes its bulged position.

At time t5, the electrical coil 72c ceases to be energized, whereby the plunger 73c is driven downward under the resilience of the thin film 60. This causes the chamber 51c to assume a negative pressure, causing the diaphragm 21c to be retracted and the fluid located on top of the diaphragm 21b to be withdrawn by the diaphragm 21c. Since the diaphragm 21d remains in its bulged position, the fluid located on top of the diaphragm 21d is not substantially attracted. At time t5, the energization of the electrical coil 72e is initiated, whereby the diaphragm 21e bulges into the fluid channel 13 in the same manner as mentioned above. Since the diaphragm 21e assumes its bulged position at this time, the fluid located on top of the diaphragm 21e is driven, substantially in its entirety, toward the second port 12.

At time t6, the arrangement returns to the same condition as prevailing at time t1. In this manner, the bulging/retracting oscillation of the diaphragms 21a–21e are repeated with one cycle extending from time t1 to time t6. The fluid being driven is withdrawn from the first port 11 and is delivered through the second port 12. Adjacent diaphragms are sequentially driven for bulging operation with a time difference therebetween, but there is a time period during which the both diaphragms are bulging simultaneously. Considering three adjacent diaphragms, when a central diaphragm is bulging, a diaphragm which is located downstream or located nearer the second port 12, as viewed in the direction in which the fluid is being driven, is switched to its bulging action while a diaphragm located upstream, or located nearer the first port 11, is switched to its retracting action, so that a positive pressure (discharge pressure) which results from the bulging action of the downstream diaphragm does not substantially propagate to the upstream side while a negative pressure (a suction) which results from the retracting action of the upstream diaphragm does not substantially propagate to the downstream side, whereby the efficiency of delivery of fluid being driven by the oscillation of the diaphragms remains high. When the resistance of the potentiometer 95 is changed, the period of the pulse A generated by the pulse generator 94 changes to a longer or shorter one, whereby the cycle time (time t6–t1) becomes longer or shorter. When the period or the cycle time becomes longer, the delivery rate (flow rate per unit time) is reduced while when the period of the cycle time becomes shorter, the delivery rate increases, and thus the delivery rate can be adjusted by means of the potentiometer 95.

With the energization circuit shown in FIG. 4, the duty cycle of energization or the duration of energization within one cycle divided by one cycle time multiplied by 100 (in %) is equal to 40% (or 2×100/5) and this cannot be changed. In a modification, an energization circuit which permits the duty cycle of energization to be changed is employed. By way of example, the energization control circuit 100 is replaced by a computerized control circuit essentially comprising CPU and numerical input board. Again, considering three adjacent diaphragms, when a center diaphragm is bulging, it is favorable for purpose of driving efficiency to choose a duty cycle of energization in a range which is centered at $2 \times 100/n$ % (where n represents the number of diaphragms juxtaposed, and n=5 in the first embodiment) and which is greater than $1 \times 100/n$ % and less than $3 \times 100/n$ %, so that, the upstream diaphragm is switched to its retracting action while the downstream diaphragm is switched to is bulging action even though there is a time difference therebetween. Since the delivery rate reaches its peak when the duty cycle of energization is equal to $2 \times 100/n$ %, and the delivery rate is substantially halved when the duty cycle is equal to $1 \times 100/n$ % and $3 \times 100/n$ %, respectively, the delivery rate may be roughly established by choosing the cycle time and may be finely adjusted by adjusting the duty cycle in a range from $1 \times 100/n$ % to $2 \times 100/n$ %. In this manner, a more fine adjustment of the delivery rate is possible.

Since the flow-through groove 13 in the channel member 10 has a cross section, taken in an orthogonal direction with respect to the length thereof, which exhibits a curved bottom surface conforming to the bulging configuration of the diaphragms 21a–21e, it will be seen that the diaphragms bulge in a manner to close the flow-through groove 13. Accordingly, there is substantially no clearance between the bulging diaphragm and the bottom surface of the flow-through groove 13, as viewed in the cross section, whereby an escape of the fluid being driven from the downstream side to the upstream side is avoided, assuring a positive feed of fluid being driven in response to the oscillation of the diaphragm. In other words, a high delivery efficiency is maintained.

Second Embodiment

Figure 6:
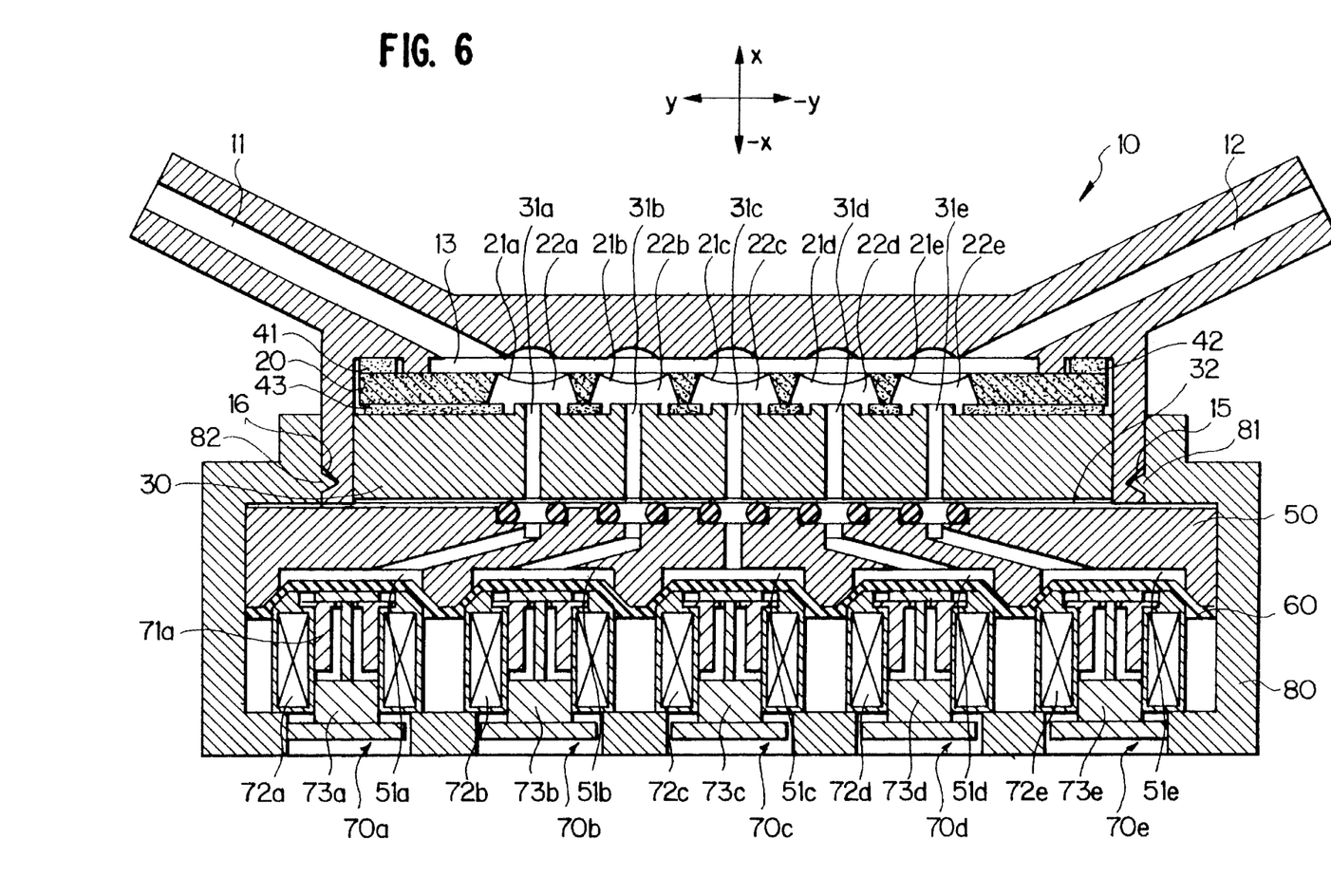
FIG. 6 is a longitudinal section of a pump mechanism according to a second embodiment of the invention.

FIG. 6 shows a pump mechanism according to a second embodiment of the invention in which the configuration of the channel member 10 is slightly modified from that of the first embodiment. Specifically, the bottom surface of the fluid channel 13 is generally planar, but at locations opposite to the diaphragms, is formed with grooves 14 each having a circular edge and a bottom surface which is in the form of part of a sphere for receiving spherical top of a diaphragm as it bulges. In other respects, the construction is substantially identical to that of the first embodiment.

Third Embodiment

Figure 7:
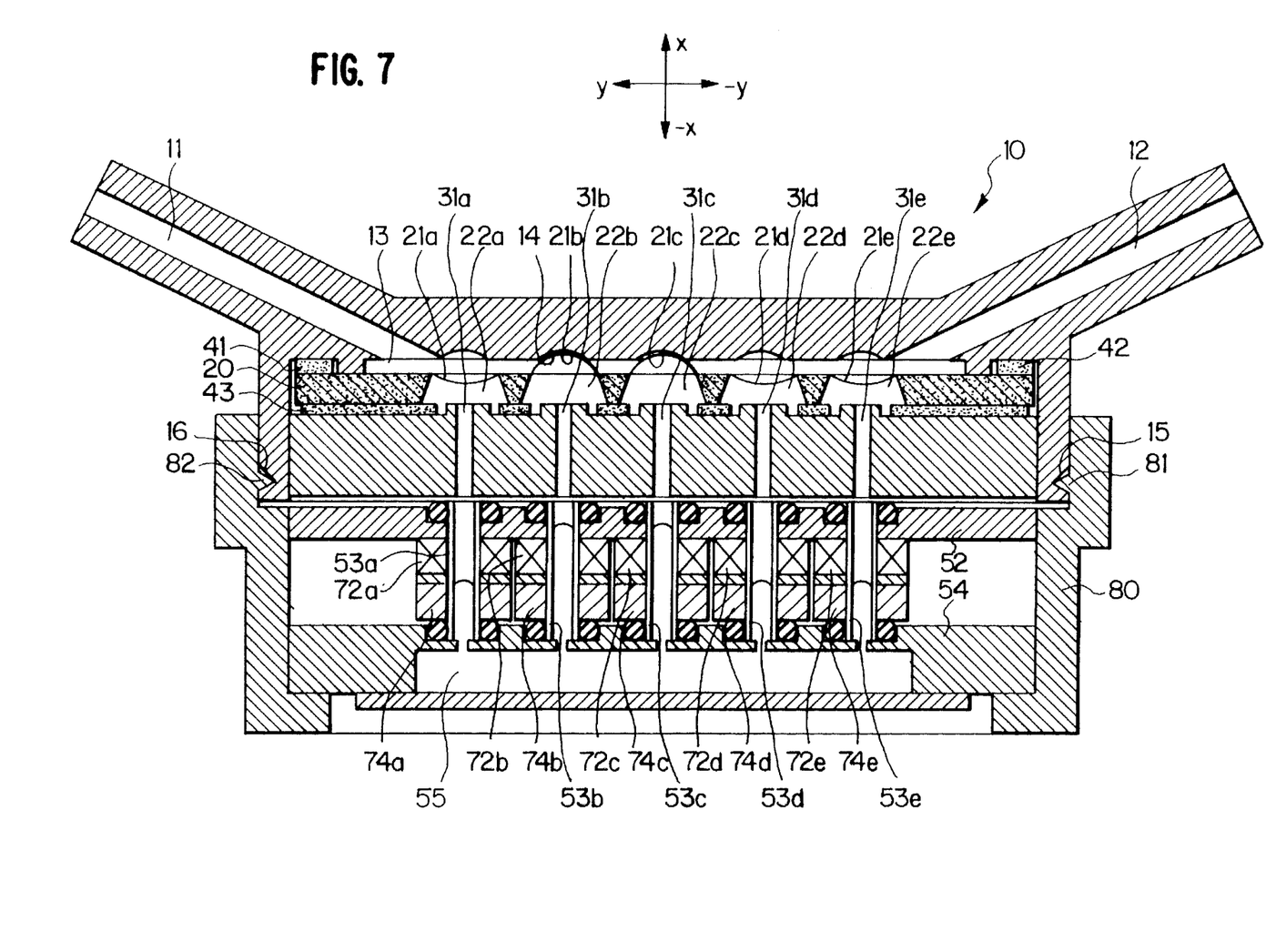
FIG. 7 is a longitudinal section of a pump mechanism according to a third embodiment of the invention.

FIG. 7 shows a pump mechanism according to a third embodiment of the invention. In the third embodiment, a channel member 10, and a silicon plate 20 and an upper relay plate 30 which are received in the channel member are constructed in the same manner as mentioned above in connection with the second embodiment. In the third embodiment, tubes 53a–53e, communicating with the gas passages 31a–31e in the upper relay plate 30, are fixedly mounted in a lower relay plate 52, and the lower ends of these tubes 53a–53e are supported by a support plate 54, which is hollow and the hollow space communicates with the internal space within the tubes 53a–53e. A magnetic fluid 55 is received in the internal space of the support plate 54 and the tubes 53a–53e. Each of the tubes 53a–53e has mounted thereon one of electrical coils 72a–72e and one of ring-shaped permanent magnets 74a–74e. Considering the tube 53a as an example, the tube 53a extends through the central bores formed within the ring-shaped permanent magnet 74a and the electrical coil 72a. The magnets 74a–74e are magnetized in the direction in which each tube 53a–53e extends. Alternatively, such magnet may be magnetized in the radial direction.

When electrical coils 72b and 72c are energized, the magnetic force generated by them pull up the magnetic fluid 55 from within the tubes 53b and 53c, whereby the diaphragms 21b and 21c bulge as shown in FIG. 7. The sum of quantity of magnetic fluid within the support plate 54 and the tubes 53a–53e is constant, as a matter of course, and accordingly when the amount of magnetic fluid within the tubes 53b and 53c increase, the remaining sum of magnetic fluid in the other tubes decrease by a corresponding amount. The coils 72a–72e shown in FIG. 7 are energized by an electrical circuit as shown in FIG. 4, in the same manner as in the first embodiment. Accordingly, the diaphragms 72a–72e operate in the same manner as described above in connection with the first embodiment. In the third embodiment, the plungers initially used are replaced by the magnetic fluid. By way of example, FIG. 7 illustrates a condition assumed during an interval from time t3 to time t4 shown in FIG. 5, and it will be noted that at time t4, the coil 72b ceases to be energized while the coil 72d begins to be energized, so that the magnetic fluid within the tube 53d is pulled up while the magnetic fluid within the tube 53b descends in a complementary manner to each other, so that the power required to drive the magnetic fluid is saved, thus reducing a power loss. In other respects, the function, the effect and the possible modifications are similar to those described above in connection with the first embodiment.

Fourth Embodiment

Figure 8:
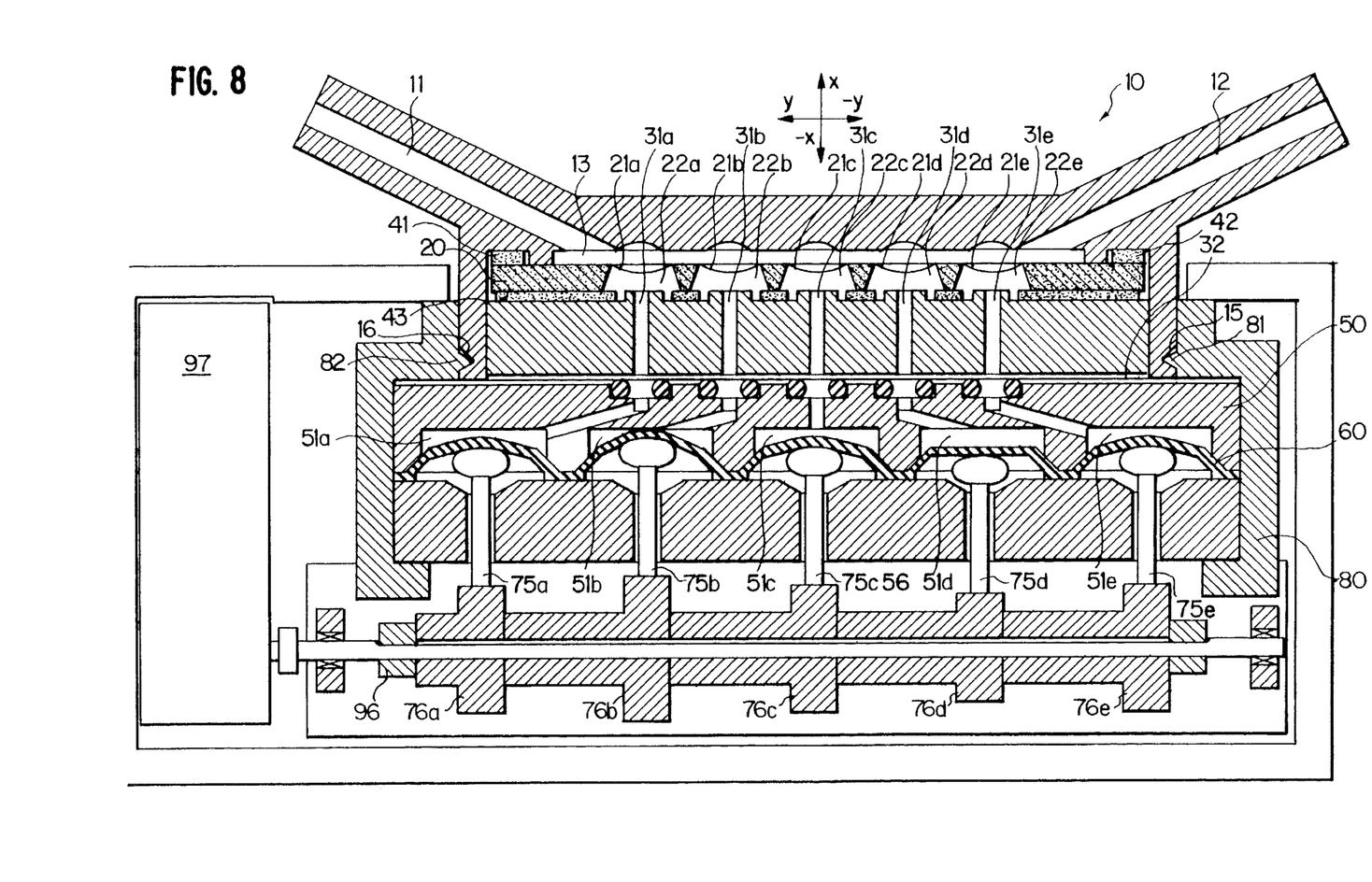
FIG. 8 is a longitudinal section of a pump mechanism according to a fourth embodiment of the invention.

FIG. 8 shows a pump mechanism according to a fourth embodiment of the invention. A channel member 10 as well as a silicon plate 20, an upper and a lower relay plate 30, 50 and a thin film 60 in this fourth embodiment are constructed in the same manner as mentioned above in connection with the second embodiment. In this embodiment, a plurality of push rods 75a–75e are supported by a guide plate 56 so as to be vertically movable, and have their upper end faces disposed in abutment against a thin film 60. The lower end face of each of the push rods 75a–75e is disposed in abutment against a corresponding one of cams 76a–76e having a peripheral surface which is shaped in the form of a rice-ball. The cams 76a–76e are fixedly mounted on a rotary shaft. The cams 76a–76e have peripheral surfaces of an identical configuration, but they are fixedly mounted on the rotary shaft 96 so that there is a phase difference of 72° between adjacent cams. The rotary shaft 96 is connected to an output shaft of a flat electric motor unit 97 internally housing a reduction gearing. The shaft 96 is driven for clockwise rotation, as viewed from the side of the motor unit 97. Under the condition illustrated in FIG. 8, the cam 76b has its crest aligned on a line with the rod 75b, whereby the latter is located at its upper dead center. The cam 76a is advanced 72° clockwise with respect to the cam 76b while the cam 76c is lagging 72° clockwise with respect to the cam 76b. The cam 76d is lagging 72° clockwise with respect to the cam 76c, with its minor axis aligned on a line with the rod 75d, whereby the rod 75d is located at its lower dead center. The cam 76e is lagging 72° clockwise with respect to the cam 76d. In this manner, the cams 75a–75e are mounted so that they are sequentially lagging by an angle of 72° in the clockwise direction.

Accordingly, when the rotary shaft 96 rotates through 72° clockwise from the condition shown in FIG. 8, the rod 75a descends to its lower dead center, and during such process, the diaphragm 21a retracts to withdraw the fluid being driven from the first port 11. The rod 75b descends through half its reciprocating stroke, and during such process, the diaphragm 21b begins to retract, initiating withdrawal of the fluid being driven. The rod 75c reaches its upper dead center, and during such process, the diaphragm 21c drives the fluid. The rod 75d rises through half its reciprocating stroke, and during such process, the diaphragm 21b begins to bulge, initiating to drive the fluid. The rod 75e reaches its upper dead center, and during such process, the diaphragm 21e delivers the fluid through the second port, and then it comes to a stop. In this manner, as the rotary shaft 76 rotates clockwise in response to the motor 97, successive ones of the rods 75a–75e reach their upper dead center in a sequential order beginning from one located nearest the first port 11 and shifting toward another located nearest the second port 12. In the similar manner, the diaphragms 21a–21e bulge sequentially, whereby the fluid is withdrawn from the first port 11, and the fluid disposed within the fluid channel 13 is gradually delivered through the second port 12. During one revolution of the rotary shaft 96, the rods 75a–75e complete two reciprocating cycles. In other words, the diaphragms 21a–21e perform two cycles of feeding oscillations. When the rotational speed of the motor 97 is increased, the number of repetitions, as measured per unit time, of the feeding oscillations increase, whereby the delivery rate of the fluid increases. In other respects, the function and the effects are similar to those described above in connection with the second embodiment.

While preferred embodiments have been shown and described, it should be understood that a number of changes and modifications are possible therein, and accordingly it is to be understood that there is no intention to limit the invention to the precise construction disclosed herein, and the right is reserved to all changes and modifications coming within the scope of the invention as defined in the appended claims.

What is claimed is:

1. Pneumatically driven micro-pump comprising channel means including a first port, a second port and a flow-through space which provides a communication therebetween;

a plurality of diaphragms disposed in an array along the flow-through space in a direction from the first to the second port and each having its front surface exposed to the flow-through space and capable of bulging/retracting with respect to the space;

diaphragm support means disposed on the opposite side of the diaphragms from the flow-through space and including a plurality of actuating gas spaces which are disposed in opposing relationship with the rear surfaces of the respective diaphragms;

a plurality of reciprocatory motion means for individually imparting a pneumatic oscillation to the respective actuating gas spaces;

and drive means for driving each of the reciprocatory motion means for reciprocatory motion with phase differences therebetween such that the reciprocatory motion means which reaches its upper dead center where a high pressure peak is applied to its associated actuating gas space shifts sequentially in a direction from the first to the second port.

2. Pneumatically driven micro-pump according to claim 1 in which the flow-through space comprises an internal space in the form of a flow-through channel which provides a communication between the first and the second port and which has a curved bottom surface which conforms to the configuration of the diaphragm as it bulges when viewed in a cross section perpendicular to the longitudinal direction of the channel.

3. Pneumatically driven micro-pump according to claim 2 in which the bottom surface of the flow-through channel is arcuate, forming part of a cylinder, when viewed in its cross section, and is linearly flat as viewed in the longitudinal direction of the channel.

4. Pneumatically driven micro-pump according to claim 1 in which the diaphragm support means includes fine gas venting paths communicating with the actuating gas spaces.

5. Pneumatically driven micro-pump according to claim 1 in which the diaphragm support means comprises a silicon plate, and the diaphragm is formed of a material having a coefficient of thermal expansion which is less than the coefficient of thermal expansion of the silicon plate.

6. Pneumatically driven micro-pump according to claim 5 in which the diaphragm includes an $SiO_2$ layer which is formed in a high temperature environment.

7. Pneumatically driven micro-pump comprising channel means including a first port, a second port and a flow-through space which provides a communication therebetween;

a plurality of diaphragms disposed in an array along the flow-through space in a direction from the first to the second port and each having its front surface exposed to the flow-through space and capable of bulging/retracting with respect to the space;

diaphragm support means disposed on the opposite side of the diaphragms from the flow-through space and including a plurality of actuating gas spaces which are disposed in opposing relationship with the rear surfaces of the respective diaphragms;

an elastic thin film for individually imparting an oscillation of pneumatic pressure to each of the actuating gas spaces;

a plurality of solenoids individually associated with each of the actuating gas spaces and each including a plunger disposed for abutment against the elastic thin film and an electrical coil for driving the plunger to project to induce the oscillation of pneumatic pressure;

a plurality of solenoid drivers for individually energizing the solenoids;

and energization control means for applying energizing signals to the plurality of solenoid drivers with phase differences therebetween such that the plungers of the plurality of solenoids reach their respective upper dead center where a high pressure peak is imparted to the associated actuating gas space in a sequence which shifts in a direction from the first to the second port.

8. Pneumatically driven micro-pump according to claim 7 in which the diaphragm support means includes fine gas venting paths communicating with the actuating gas spaces.

9. Pneumatically driven micro-pump according to claim 7 in which the diaphragm support means comprises a silicon plate, and the diaphragms are formed of a material having a coefficient of thermal expansion which is less than that of the silicon plate.

10. Pneumatically driven micro-pump according to claim 9 in which the diaphragms include an $SiO_2$ layer which is formed in a high temperature environment.

11. Pneumatically driven micro-pump comprising channel means including a first port, a second port and a flow-through space providing a communication therebetween;

a plurality of diaphragms disposed in an array along the flow-through space in a direction from the first to the second port and each having its front surface exposed to the flow-through space and capable of bulging/retracting with respect to the space;

diaphragm support means disposed on the opposite side of the diaphragms from the flow-through space and including a plurality of actuating gas spaces which are disposed in opposing relationship with the rear surfaces of the respective diaphragms;

a magnetic body received in each space communicating with the respective actuating gas spaces so as to be movable in a direction toward and away from the actuating gas spaces;

a plurality of magnetic drive means each including an electrical coil for driving the magnetic body in a direction to reduce the volume of the space communicating with the respective actuating gas space and a magnet driving the magnetic body in the opposite direction;

a plurality of solenoid drivers for individually energizing the electrical coils;

and energization control means for applying energizing signals to the plurality of solenoid drivers with phase differences therebetween such that the magnetic body driven by the respective electrical coils of the plurality of magnetic drive means reaches an upper dead center where a high pressure peak is imparted to the associated actuating gas space in a sequence which shifts in a direction from the first to the second port.

12. Pneumatically driven micro-pump according to claim 11 in which the diaphragm support means includes fine gas venting paths communicating with the actuating gas spaces.

13. Pneumatically driven micro-pump according to claim 11 in which the diaphragm support means comprises a silicon plate, and the diaphragms are formed of a material having a coefficient of thermal expansion which is less than that of the silicon plate.

14. Pneumatically driven micro-pump according to claim 13 in which the diaphragms include an $SiO_2$ layer which is formed in a high temperature environment.

15. Pneumatically driven micro-pump comprising channel means including a first port, a second port and a flow-through space providing a communication therebetween;

a plurality of diaphragms disposed in an array along the flow-through space in a direction from the first to the second port and each having its front surface exposed to the flow-through space and capable of bulging/retracting with respect to the space;

diaphragm support means disposed on the opposite side of the diaphragms from the flow-through space and including a plurality of actuating gas spaces which are disposed in opposing relationship with the rear surfaces of the respective diaphragms;

an elastic thin film for individually imparting an oscillation of pneumatic pressure to each of the actuating gas spaces;

a plurality of cam/rod assemblies individually associated with the actuating gas spaces and each including a rod disposed for abutment against the elastic thin film and a cam which drives the rod to project to produce an oscillation of pneumatic pressure;

and a rotary shaft on which the cams are fixedly mounted and an electric motor for driving the rotary shaft for rotation, the cams being mounted on the rotary shaft with angular differences therebetween such that the rod which reaches an upper dead center where a high pressure peak is imparted to an associated actuating gas space sequentially shifts in a direction from the first to the second port.

16. Pneumatically driven micro-pump according to claim 15 in which the diaphragm support means includes fine gas venting paths communicating with the actuating gas spaces.

17. Pneumatically driven micro-pump according to claim 15 in which the diaphragm support means comprises a silicon plate, and the diaphragms are formed of a material having a coefficient of thermal expansion which is less than that of the silicon plate.

18. Pneumatically driven micro-pump according to claim 17 in which the diaphragms include an $SiO_2$ layer which is formed in a high temperature environment.

\* \* \* \* \*